United States Patent
Wiets

(10) Patent No.: US 11,478,202 B2
(45) Date of Patent: Oct. 25, 2022

(54) PATIENT SUPPORT DEVICE FOR AN X-RAY DEVICE AND METHOD FOR ADJUSTING A PATIENT COUCH OF A PATIENT SUPPORT DEVICE

(71) Applicant: Siemens Healthcare GmbH, Erlangen (DE)

(72) Inventor: Michael Wiets, Langensendelbach (DE)

(73) Assignee: Siemens Healthcare GmbH, Erlangen (DE)

( * ) Notice: Subject to any disclaimer, the term of this patent is extended or adjusted under 35 U.S.C. 154(b) by 169 days.

(21) Appl. No.: 16/545,156

(22) Filed: Aug. 20, 2019

(65) Prior Publication Data

US 2020/0060634 A1 Feb. 27, 2020

(30) Foreign Application Priority Data

Aug. 23, 2018 (EP) .................................... 18190507

(51) Int. Cl.
A61B 6/04 (2006.01)

(52) U.S. Cl.
CPC ............ *A61B 6/0442* (2013.01); *A61B 6/045* (2013.01)

(58) Field of Classification Search
CPC ..... A61B 6/0442; A61B 6/045; A61B 6/0407; A61B 2090/3764; A61B 6/4441;
(Continued)

(56) References Cited

U.S. PATENT DOCUMENTS 5,395,299 A * 3/1995 Herrmann ................ A61B 6/12
378/162
2010/0324433 A1 12/2010 Wilson et al.
(Continued)

FOREIGN PATENT DOCUMENTS

CN 108024900 A * 5/2018 ............ A47C 21/04
DE 3716263 A1 11/1988
(Continued)

OTHER PUBLICATIONS

Kumar, Rohitash, et al. "Development of Sodium Acetate Trihydrate-Ethylene Glycol Composite Phase Change Materials with Enhanced Thermophysical Properties for Thermal Comfort and Therapeutic Applications." Nature, Scientific Reports, Jul. 12, 2017, www.nature.com/articles/s41598-017-05310-3. (Year: 2017).*
"Vinyl." Merriam-Webster, Learner's Dictionary, www.learnersdictionary.com/definition/vinyl.*
"Pivot." Vocabulary, Vocabulary, https://www.vocabulary.com/dictionary/pivot.*
European Search Report for European Patent Application No. 18190507.6-1124 dated Feb. 14, 2019.
Wikipedia "Phase-change material" (https://en.wikipedia.org/wiki/Phase-change_material) Retrieved at https://en.wikipedia.org/wiki/Phase-change_material Accessed May 12, 2019. pp. 22.
Wikipedia, "Paraffin" ("Paraffin wax") Retrieved at https://en.wikipedia.org/wiki/Paraffin_wax Accessed May 12, 2019. pp. 1-5.
(Continued)

*Primary Examiner* — David R Hare
*Assistant Examiner* — Madison Emanski
(74) *Attorney, Agent, or Firm* — Lempia Summerfield Katz LLC

(57) ABSTRACT

Systems and methods are provided for a patient support device for an x-ray device for use during an examination of a patient including a patient couch and at least one support (6) bearing the patient couch. The patient couch includes a first, x-ray-transparent material disposed in an at least partially flexible covering made from a second x-ray-transparent material. The first material includes a solid, dimensionally stable state and a deformable state, in particular at least partially liquid and/or gaseous state, that are linked by reversible phase transitions. The patient support device further includes at least one induction device for inducing at least one of the phase transitions of the first material between the states by applying and/or removing energy.

14 Claims, 3 Drawing Sheets

(58) Field of Classification Search
CPC ... A61B 2090/376; A61B 6/485; A61B 6/487; A61B 6/00; A61B 6/02; A61B 6/04; A61B 6/0487; A61B 90/30; A61B 90/37; A61B 6/12; A61G 2210/90; A61G 2210/50; A61G 2203/30; A61G 2203/46
See application file for complete search history.

(56) References Cited

U.S. PATENT DOCUMENTS

| | | |
|---|---|---|
| 2015/0107601 A1 | 4/2015 | Arnone et al. |
| 2017/0135884 A1 | 5/2017 | Lachenbruch |
| 2018/0161198 A1* | 6/2018 | Gaiser .................. A61F 7/0085 |
| 2019/0105212 A1 | 4/2019 | Verstegen et al. |

FOREIGN PATENT DOCUMENTS

| | | | |
|---|---|---|---|
| DE | 19900257 A1 | 7/2000 | |
| EP | 3167765 A1 * | 5/2017 | ............... A61B 5/01 |
| JP | S62270679 A | 11/1987 | |
| JP | H08308887 A | 11/1996 | |
| JP | 2006008760 A | 1/2006 | |
| JP | 2010517697 A | 5/2010 | |
| JP | 2018515151 A | 6/2018 | |

OTHER PUBLICATIONS

Japanese Notice of Allowance for Japanese Application No. 2019-126395 dated Jul. 7, 2021, with English translation.
Japanese Office Action for Japanese Application No. 2019-126395 dated Jun. 29, 2021, with English translation.

* cited by examiner

PATIENT SUPPORT DEVICE FOR AN X-RAY DEVICE AND METHOD FOR ADJUSTING A PATIENT COUCH OF A PATIENT SUPPORT DEVICE

CROSS REFERENCE TO RELATED APPLICATIONS

This application claims the benefit of EP18190507.6 filed on Aug. 23, 2018, which is hereby incorporated by reference in its entirety

FIELD

Embodiments relates to a patient support device for an x-ray device for use in an examination of a patient including a patient couch and at least one support bearing the patient couch.

BACKGROUND

When examinations within the scope of surgical interventions, e.g. operations, or therapy measures are carried out, a plurality of patient support devices have been used to support the patient on the one hand in a secure and stable manner, and so that an optimal positioning of the patient exists for the examination, for example, the surgical intervention. To this end, patient support devices that may also be referred to as operating tables, include adjusting devices, e.g. articulation joints between different boards of the patient couch, that provides the support surface for the patient.

Image monitoring mechanisms, such as x-ray devices, are increasingly used for surgical interventions, for example for minimally invasive interventions, e.g. operations on a patient. Examining the patient therefore forms part of the operation. For example, it has been proposed to trace the position of a minimally invasive medical instrument within a patient using fluoroscopy images of an x-ray device. An x-ray device with a C-arm may be used that may be adjusted in a plurality of recording geometries. The problem in this context, where the operating tables including multiple adjustment options as a patient support device for the x-ray device are used, is that the operating tables are not or only partially x-ray-permeable. For example, hinges that connect the individual boards of the patient couch to one another may have stainless steel, as a result of which the hinges are not x-ray transparent. Scientific examinations have shown that the dynamic of the x-ray images is negatively affected by the patient couches of the operating tables, particularly in the region of the adjusting devices, such that the anatomy of the patient may no longer be beneficially x-rayed.

To solve this problem, x-ray-transparent patient couches (tabletops) have been proposed, that then consequently have no or only very few adjustment options which may significantly hamper the operations on the patient. Ideally an operating table that may be adjusted in multiple ways namely has hinges at the respectively large joints of a patient, hinges corresponding to knee joints, hip joints, and shoulder joints. Extensions such as arm supports and/or head supports are sometimes attached. A longitudinally divisible patient couch in the leg area may be also used to be better able to perform laparoscopic interventions, for example.

BRIEF SUMMARY AND DESCRIPTION

The scope of the present invention is defined solely by the appended claims and is not affected to any degree by the statements within this summary. The present embodiments may obviate one or more of the drawbacks or limitations in the related art.

Embodiments provide a patient support device for x-ray examinations, e.g. the x-ray image monitoring in operations on a patient, that, despite the most flexible adjustability possible, also provides high-quality x-ray images to be recorded.

Embodiments include a patient couch including a first, x-ray-transparent material located in an at least partially flexible covering made from a second, x-ray-transparent material. The first material includes a solid, dimensionally stable state and a deformable state, for example, at least partially liquid and/or gaseous state, that are linked by reversible phase transitions. The patient support device further includes at least one induction device for inducing at least one of the phase transitions of the first material between the states by applying or removing energy.

Term "x-ray-transparent" may be understood broadly to refer to when a proportion of the x-ray radiation that is sufficient for an imaging measurement can pass through the first and the second material. For example, the first and/or second material may have an x-ray attenuation comparable with fat and/or water so that an adequate x-ray transparency is still provided, e.g. with the intended thicknesses of the patient couch in the range of a few centimeters, for example in the range of 2 to 7 cm. The thickness of the patient couch is at least essentially the same overall, so that the attenuation through the materials is at least essentially the same at each position.

The first material includes a solid, dimensionally stable state and a deformable state, that are linked by reversible phase transitions. When the first material is in one of the two states, it may be transferred into the other state by a phase transition. Since this is reversible, this also applies vice-versa.

In an embodiment, the patient couch connected, for example detachably, with the support, e.g. with at least one pillar, that may also be referred to as the patient board, not to be formed as previously from subplates, that receive the load of the patient, and hinges, that connect the individual subplates to one another, but instead from a continuous covering made of a second material with a first material therein, that, for example, in a suitable temperature range, passes through a phase transition that may be induced from the outside, for example from liquid to solid. The second material is expediently phase stable in the state used by the induction device for the first material. At least one of the phase transitions may also take place without induction. With a deformable state of the first material, thanks to the flexible covering, firstly to mold the patient couch in a desired manner, in order then, for example induced, to transfer the same by a phase transition into the solid, dimensionally stable state, and thus to allow the same to solidify in the predetermined form. The patient on the patient couch, that is if applicable to be fastened to the support, may then be subjected to the examination, together with or accompanying a surgical intervention, e.g. an operation. For the next patient (or another examination), a further phase transition may then be used to transfer the first material back from the solid state into the deformable state, so that a renewed form adjustment may take place.

In this way, a patient support device, that may also be referred to as a patient couch, is provided for carrying out an examination, for example together with or accompanying a surgical intervention, on a patient during x-ray monitoring, that may be flexibly adjusted to different ideal shapes for the examination and/or treatment of the patient, but still includes an x-ray transparency, that allows for excellent x-ray imaging even through the patient couch.

The patient couch may be fastened detachably to the support. The patient support device includes a detachable fastening device for fastening the patient couch to the support. The detachable fastening device may be at least partially x-ray transparent and/or use as small a fastening area as possible, e.g. less than 10% of the surface of the patient couch available for supporting the patient, or less than 5% of the surface of the patient couch available for supporting the patient. The support may include one or more pillars and/or may support the patient couch freely. With one pillar, this is disposed centrally below or in the center of gravity of the patient couch, so that the fastening the detachable fastening device located on the patient couch side are disposed centrally or in the center of gravity on the surface opposing the support area available to support the patient. With several pillars, at least one pillar may be provided at each longitudinal end of the patient couch.

In the continuous covering, e.g. the second material, the patient couch may specifically have integrated fastening the detachable fastening device, for example a plate embedded, for example cast into the supporting material and/or fastened, for example, glued to the supporting material, that offers nuts for screws in the detachable fastening device that engage herein for fastening purposes. Another example of the fastening device uses projections/profiles that may be inserted into grooves formed accordingly. Other corresponding embodiments are also possible.

In an embodiment, the first material may be viscous in the deformable state. For example, the first material may have a viscosity of greater than 100 mPas. A viscosity or high viscosity also contributes to excessively large redistributions of the first material not materializing, this thus retaining an at least essentially uniform extension across the surface of the patient couch during the deformation. Further features of the patient couch that contribute to this embodiment are discussed in more detail below.

In an embodiment, the first material may be water. At normal room temperatures, water is liquid, wherein it solidifies to ice when refrigerated. This refrigeration process may be caused by the induction device, for example. The covering may be heat insulating. A slight undercooling may also be advantageous with many types of operations.

In an embodiment, the first material may include or be a latent heat storage material, e.g. sodium acetate trihydrate and/or another paraffin and/or a PCM wax. Latent heat storage materials are also known as phase change materials (PCM) and are used in what are known as handwarmers, for example, and include a phase transition between a viscous and a crystallized, solid state. Latent heat storage materials such as paraffin, for example sodium acetate trihydrate, and/or PCM wax are phase change materials, in which the induction of a phase transition may be achieved easily in at least one direction. In the example of sodium acetate trihydrate, this includes a melting temperature of 58° C., so that by heating the patient couch to this temperature, the viscous state may be induced, that, even at temperatures far below the melting point, in some examples as far as −20, remains as undercooled melted mass in a metastable state, since the salt dissolves in its water of crystallization. If a crystallization triggering apparatus, for example a click plate and/or a piezo element is used as the induction device, the crystallization may be triggered. However, the patient couch then heats up again and the patient support device includes a heat discharge device/cooling device in order to discharge heat produced during the solidification process. An elastically extendible second material of the covering may be used, since for example paraffins have a volume change of approx. 10 to 30% during a phase transition from solid to liquid, that has to be taken into account when the second material of the covering is selected.

Another latent heat storage material aside from the sodium acetate trihydrate, that is suitable, is what is known as a PCM wax, for example the material marketed under the name RT25 by the company Rubitherm Technologies GmbH, Berlin, Germany. This includes a suitable melting point of approx. 22-26° C.

In an embodiment, a foam as a first material or a first material including a foam is used. Foam is suitable as a substrate, into which a latent heat storage material may be embedded; this is also the subject matter of ongoing research. Foams may influence the heat storage and heat discharge properties in a regulating manner and thus may be used beneficially in which the heat storage property is less significant.

In another embodiment, the first material is or includes a liquid, that changes its viscosity under the influence of an electrical and/or magnetic field. Such liquids are also referred to as electrorheological or magnetorheological liquids. The induction device may include a corresponding field generator, for example.

At least one plastic may be used as the second material and/or the second material may include at least one plastic. Suitable plastics, that have the requisite flexibility and possibly elasticity as well as being phase stable in the relevant operational area, are already known.

In an embodiment, the first material and the second material include the same attenuation properties for x-ray radiation. Transitions of different attenuation properties, that may lead to refraction and/or other effects, are avoided as far as possible and the minimal influence on the patient couch as a result of the x-ray transparency is further reduced. Artifacts in the imaging are minimized.

In an embodiment, the second material may be elastic to compensate for a change in volume occurring in the phase transitions and/or to promote an equal distribution of a material strength of the first material and/or to have at least one web embodied for form stabilization and having through openings for the first material and/or only to be flexible at target hinge points. Honeycombs limited correspondingly by webs may develop, that may have a size in the range of 20 to 40 mm, for example 30 mm. The honeycombs may be embodied hexagonally and may include openings.

Since some usable, useful first materials in the phase transitions may have volume changes, a specific elasticity of the first material may be provided that compensates for this. An elasticity may be used to go back to a specific thickness of the patient couch, thus, to keep the overall thickness over the surface as constant as possible.

Within the covering, at least one web may be provided for form stabilization and including through openings for the first material. Such stabilizing webs that still allow for an exchange of the first material are known for example from the field of inflatable mattresses. In an exemplary embodiment, according to which changes in shape of the patient couch are to occur mainly along the longitudinal direction of the patient couch, provision may be made for example to provide webs in the transverse direction in the regions of the patient couch in which a brief loss of flexibility is less relevant. Naturally, webs covering only one part of the patient couch in the transverse direction are also possible if changes in shape are desired in the transverse direction.

In another embodiment, the second material is only flexible at target hinge points, e.g. points at which a deformation may occur are fixed from the outset. Outside of the target hinge points, the first material is selected to be inflexible so that a uniform thickness of the patient couch is also provided. In an embodiment, the second material differs across the extent of the patient couch.

In an embodiment, the induction device may generate the application and removal of energy by heat and/or cold and/or electrical current. For example, the induction device may be a heating device and/or cooling device and/or crystallization triggering device, for example, click plate and/or piezo element, and/or current feed device, the latter including at least two electrodes. With a first material to be melted, a heating device may be used as an induction device to supply sufficient heat, for example. Accordingly, a cooling device may also be provided with the reverse phase transition as a possible further induction device. Crystallization triggering devices may be useful if first materials, for example paraffin, solidifying in a crystallized manner, induced using heat discharge for example, are to be used. The embodiments as click plates and/or piezo element known from heat pads may be used, for example. If the first material outputs heat for solidification purposes, a cooling device may also be provided as a heat discharge device in addition to the crystallization triggering device.

In an embodiment, provision may be made for the patient support device to include a preparation device for the patient couch, where the preparation device includes:

at least one contact surface for the patient couch and
at least one adjusting device acting on the contact surface.

The contact surface may be adjusted in terms of extent to the extent of the patient couch. If the patient couch with the first material in a deformable state is attached to the contact surface, the adjusting devices of the preparation device may be used to cause deformations in the patient couch in a targeted and defined manner. The adjusting devices may be provided for example for adjustability purposes to all positions that are useful for operations on the patient, that are to be monitored using x-rays.

In an embodiment, at least one of the at least one adjusting device may be a hinge for tilting a portion of the contact surface against an adjacent portion of the contact surface. Other embodiments of the adjusting device are naturally also possible, however.

The preparation device may be an operating table or a frame. An (at least partially non-x-ray-transparent) operating table is advantageous. The operating table may also be prepared with the actual patient, after which a type of "impression" of the settings of the operating table may be taken with the aid of the patient couch. The adjustment options of the operating table may thus take over on the patient support at the x-ray device, where the x-ray transparency is additionally produced.

A frame may also be provided as a preparation device, that with significantly fewer demands on mechanical robustness and stability, may still have the different deformation options desired for the patient couch. For example, typical adjustment options for operating tables may be implemented in the frame, for example adjustment devices that correspond in terms of position to the joints of the patient.

The patient couch, in a leg region provided for supporting the legs of the patient, includes a cut that runs in the longitudinal direction for independently positioning the bearing surface for the respective legs of a patient in the deformable state. Below the position of the hip joint of the patient, the patient couch may be divided into two in the transverse direction, so that a cut is provided in the longitudinal direction, so that it is possible to set different positions for the different legs of the patient during the molding in the deformable state, for example to support a leg at an angle downward, that may be advantageous in the case of a laparoscopy. Another example relates to the spread support of the legs. At least one leg is supported laterally at an angle. In addition to the cut in the longitudinal direction, e.g. adjoining its end, at least one cut may also be provided in the transverse direction. If provided, the preparation device may have corresponding adjusting devices for the respective leg parts of the patient couch.

Options for positioning, therefore specifically adjusting devices, may incidentally likewise be provided on the support. The support may include where at least one pillar is adjustable at least in terms of its height. A further adjustment to the specific operation circumstances may take place. Other possible adjusting devices may also enable a tilting of the patient couch.

In respect of examinations within the scope of an operation and/or therapy, the patient support device, e.g. the patient couch, may also have typical fixing capabilities for fixing the patient.

Aside from the patient support device, embodiments also include a method for adjusting the patient couch of such a patient support device, that includes the following steps:

producing the deformable state of the second material, for example, by inducing a phase transition, deforming the patient couch, for example, in a state triggered by the support, establishing the fixed state of the second material, for example, by inducing a phase transition.

All embodiments with respect to the patient support device may be transmitted similarly to the method.

For example, a preparation device may also be used in the inventive method, where the patient couch is firstly detached from the support by the detachable fastening device, the patient couch is positioned on the contact surface of the preparation device and the deformability is carried out with the aid of the adjusting device. Once the fixed state of the second material, for example by using an induction device, has been reestablished, the patient couch may be fastened again to the support by the detachable fastening device. It is then possible to position the patient and to begin the operation on the patient, that may be monitored with high quality by the x-ray device on account of the x-ray transparency of the patient couch.

In at least in some embodiments the phase transition is induced in just one direction; for example, with water as the first material, the patient couch may finally "automatically" defrost again after use and the first material goes back into the deformable state.

BRIEF DESCRIPTION OF THE FIGURES

Further advantages and details are presented in the exemplary embodiments described below, and with reference to the drawings, in which.

DETAILED DESCRIPTION

Figure 1:
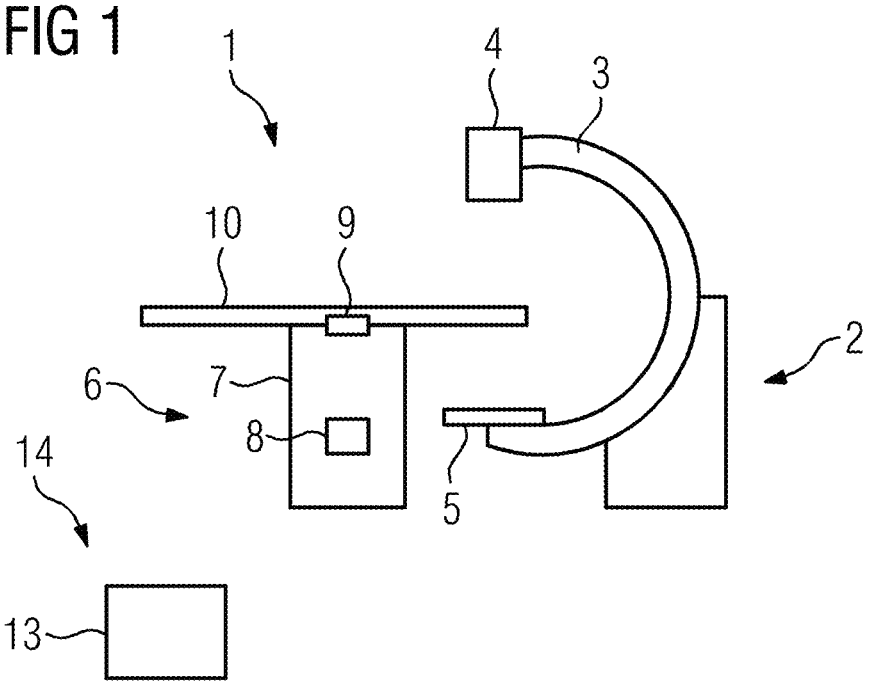
FIG. 1 depicts a patient support device with an x-ray device according to an embodiment.
Figure 1:
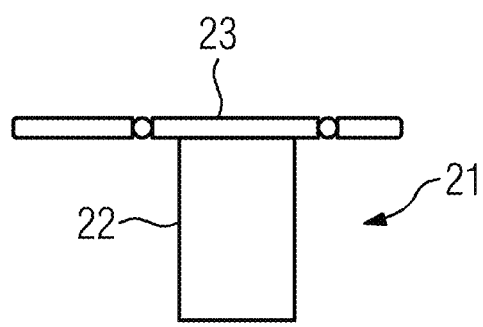

FIG. 1 shows a schematic diagram of essential components of a support device 1, that is to be used during an operation on a patient, in other words a surgical intervention, using x-ray monitoring by an x-ray device 2 likewise indicated here. The x-ray device 2 is depicted an x-ray device 2 with a C-arm 3, on which an x-ray emitter 4 and an x-ray detector 5 are arranged opposingly.

The patient support device 1 includes a support 6 fixedly installed in the region of the x-ray device 2, depicted in the form of a single, central pillar 7. The support 6 is height adjustable using a suitable adjusting device 8.

Figure 2:
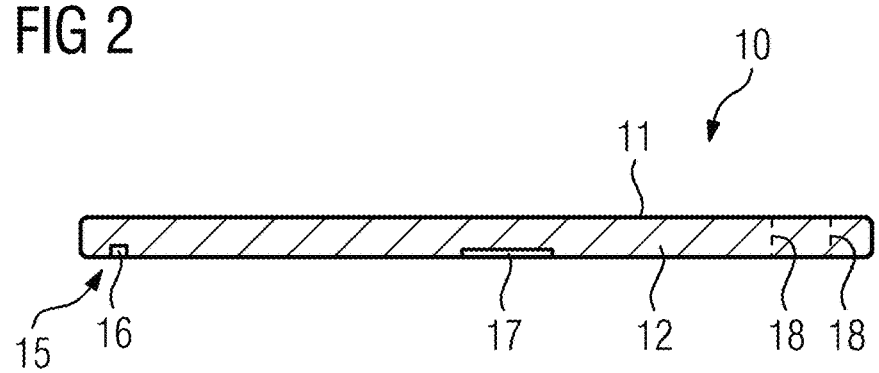
FIG. 2 depicts a patient couch of the patient support device in a cross-section according to an embodiment.

Shown fastened to the support 6 by way of a suitable, detachable fastening device 9 is a patient couch 10 that, according to the cross-sectional representation in FIG. 2, includes a covering 11 including of a second, flexible material, e.g. plastic, that, in the present example, includes or is sodium acetate trihydrate. The first material then currently performs, in the extended room temperature range, a phase transition from a fixed, solidified, here crystalline state, into a viscous, deformable state, for which reason the patient support device 1 also includes a heating device 13 indicated in FIG. 1 as an induction device 14. A second induction device 15 is provided here as a crystallization triggering device 16, for example a piezo element and/or a click plate, within the covering 11 made from the second material, e.g. plastic. The use of the first induction device 14 enables the patient couch 10 to heat up above the melting point of the first material 12, here therefore above 58° C., so that the first material 12 passes from the fixed state into the deformable state. The first material 12 currently remains in a metastable, deformable, viscous state, even when cooled to below the melting point. Only when the second induction device 15 is actuated will the phase transition be induced back into the fixed state, wherein a specific heat discharge currently takes place, that may be captured by a heat absorbing device, in particular a cooling device, to promote as rapid a solidification of the first material 12 as possible.

FIG. 2 moreover shows fastening device 17 indicated as part of the detachable fastening device 9, that may have, for example, a plate with nuts integrated into the second material of the covering 11.

The second material of the covering 11 is also embodied to be elastic, in order on the one hand to be able to compensate for the change in volume occurring in the first material 12 during the phase transitions, on the other hand the elasticity of the second material of the covering 11 also works toward maintaining as uniform a thickness across the extent of the patient couch 10 as possible. The second material may not undergo any phase changes in a range of conditions that are used by the at least one induction device to induce phase transitions in the first material.

To this end, webs 18 that are incidentally also indicated with dashed lines and that run transversely may optionally be used with through openings for the first material 12, that further stabilize the shape and thus the thickness of the patient couch 10, such as is known for example from the technology of inflatable mattresses.

Both the first material 12 and the second material include comparable x-ray attenuation properties. The second material is selected such that it is phase stable in the state variable range used for the phase transitions of the first material 12. Both the first material 12 and the second material are x-ray transparent, e.g. with the existing thickness of the patient couch 10, there is no notable x-ray attenuation that influences the x-ray imaging with the x-ray device 2.

It should be noted that other first materials 12 may also be used, for examples, mixtures of materials such as foams.

Figure 3:
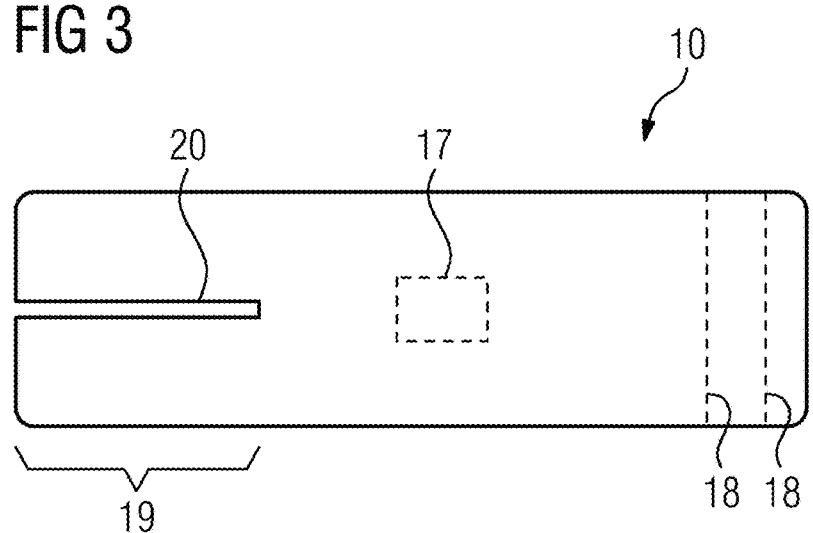
FIG. 3 depicts a view onto the patient couch according to an embodiment.

As the view onto the patient couch 10 shown in FIG. 3 depicts, this includes a cut 20 that runs in the longitudinal direction in the leg region 19 provided for the legs of the patient. Should it also be possible to spread the legs within the sense of at least one leg being supported in a laterally (right/left) angled manner, at least one cut that runs in the transverse direction may additionally be present (not shown in FIG. 3).

Figure 4:
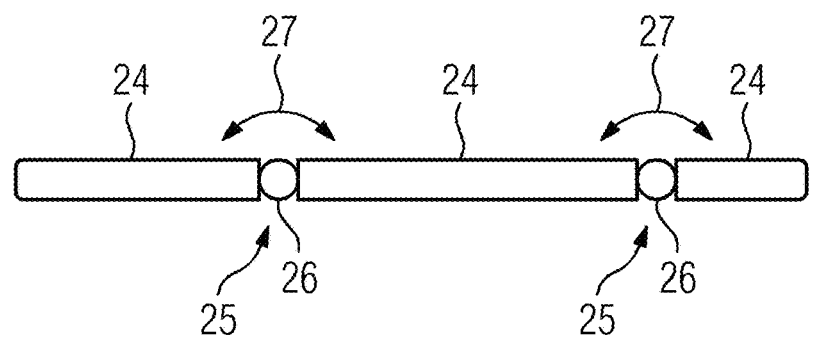
FIG. 4 depicts a side view of a contact surface of a frame of the patient support device according to an embodiment.
Figure 5:
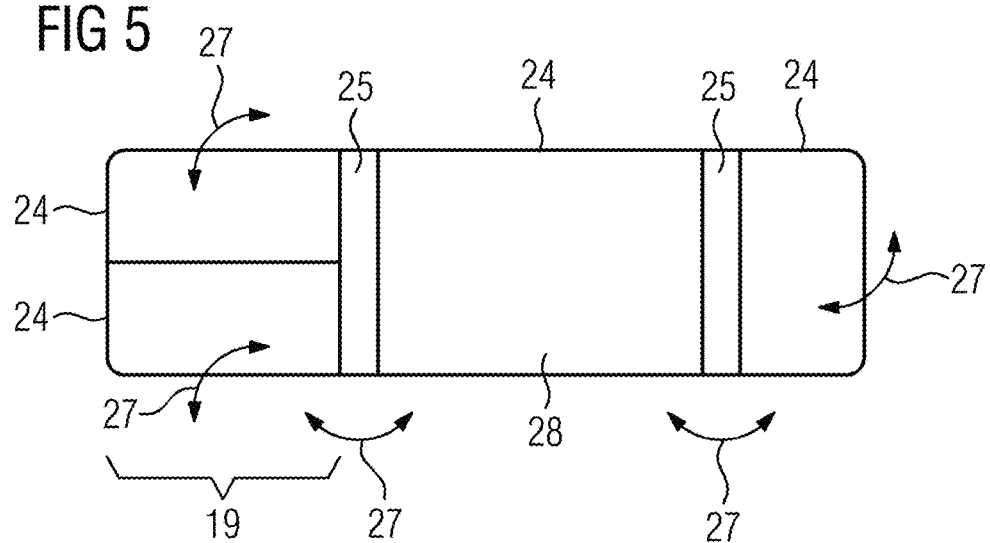
FIG. 5 depicts a top view onto the contact surface according to an embodiment.

The deformability of the first material 12 together with the flexibility of the covering 11 in the deformable state provides for the patient couch 10 to be adjusted to the current patient to be operated on or specifically the operation to be carried out. To simplify the adjustment, the patient support device 1 includes a preparation device 21 in the shape of a frame 22, that is shown in FIG. 1. The contact surface 23 of the frame 22 is shown in FIGS. 4 and 5 in a side view or a top view. The contact surface at present includes a plurality of subplates 24, that are adjustably connected by way of adjusting devices 25 that have a hinge 26, as indicated by the arrows 27. In this way only two hinge points are currently shown in the longitudinal direction since it is precisely the largely deformable embodiment of the patient couch 10 that naturally also allows for significantly more adjustment options. One example of this would also be the adjustment to the body size. For example, the middle subplate 24 may be adjustable in terms of width, since the flexible covering 11 may be angled arbitrarily. Another further option would be to spread the legs.

Figure 6:
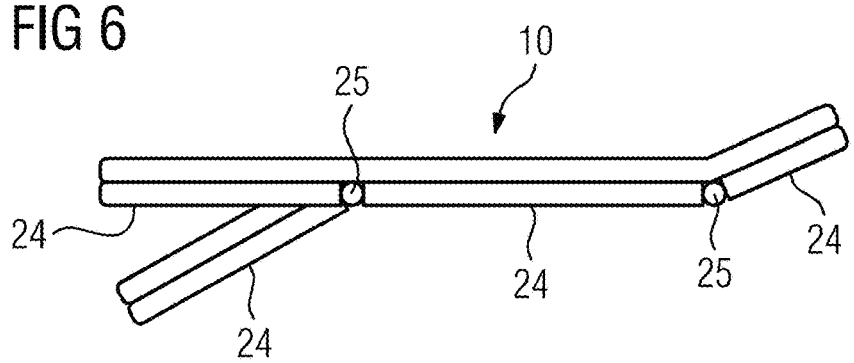
FIG. 6 depicts a representation for adjusting the patient couch according to an embodiment.

In their entirety the subplates 24 form a contact surface 28 for the patient couch 10. If the patient couch 10 with the first material 12 is placed in the deformable state on the contact surface 28, it may be adjusted suitably in terms of its shape by the adjusting devices 25, as shown in FIG. 6. Since two subplates 24 are present in the leg region 19, that may be tilted independently, different settings may be selected for both legs of the patient, as also occurs in FIG. 6.

Figure 7:
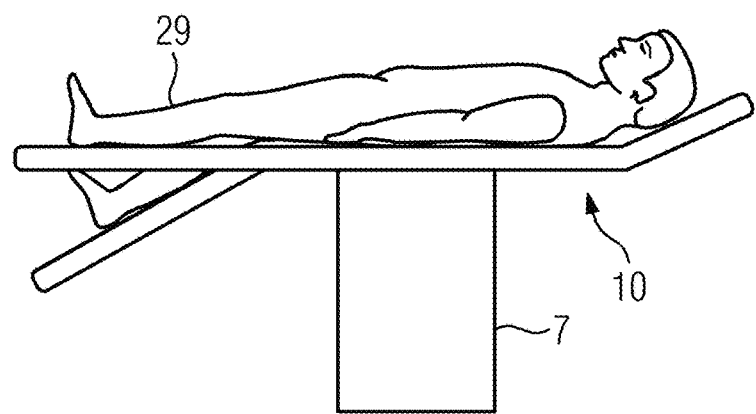
FIG. 7 depicts the adjusted patient couch in use as a patient table according to an embodiment.

After adjusting the shape of the patient couch 10, currently using the induction device 15, a phase transition back into the fixed state of the first material 12 is affected. Once this has been achieved, as shown in FIG. 7, the patient couch 10 may be fastened back onto the pillar 7 using the detachable fastening device 9 and, since the patient couch 10 is dimensionally stable, the patient 29 may be positioned thereupon.

As has already been mentioned, within the scope of the present invention, other first materials and thus also other types of induction devices are also possible. For example, the first material may include a foam. The foam may be a carrier material for a latent heat storage material, for example, where the foam may act in a modifying manner on the energy budget of the first material. For example, a quicker heat output, for example to a heat discharge device, may be favored.

Although the invention has been illustrated and described in detail with the preferred exemplary embodiment, the invention is not restricted by the examples disclosed and other variations may be derived therefrom by a person skilled in the art without departing from the protective scope of the invention.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A patient support device for an x-ray device for use during an examination of a patient, the patient support device comprising:
   a patient couch comprising a first x-ray-transparent material disposed in an at least partially flexible covering made from a second x-ray-transparent material; and
   at least one support bearing the patient couch;
   wherein the first x-ray-transparent material includes a solid, dimensionally stable state and a deformable state that are linked by reversible phase transitions;
   wherein the patient support device further comprises at least one induction device configured to induce at least one of the reversible phase transitions of the first x-ray-transparent material between the states by applying, removing, or applying and removing energy;
   wherein the at least one induction device is configured to induce a phase transition to the deformable state to mold the patient couch in a desired form and then induce a second phase transition into the solid, dimensionally stable state, to allow the patient couch to solidify in the desired form.

2. The patient support device of claim 1, wherein the deformable state is at least a partially liquid or gaseous state.

3. The patient support device of claim 1, wherein the second x-ray-transparent material does not undergo any phase changes in a range of conditions that are used by the at least one induction device to induce phase transitions in the first x-ray-transparent material.

4. The patient support device of claim 1, wherein the first x-ray-transparent material in the deformable state is viscous and comprises at least one of water, a latent heat storage material, or a foam.

5. The patient support device of claim 1, wherein the first x-ray-transparent material in the deformable state is viscous and comprises at least a latent heat storage material, specifically sodium acetate trihydrate.

6. The patient support device of claim 4, wherein the second x-ray-transparent material comprises at least one plastic or is a plastic.

7. The patient support device of claim 1, wherein the first x-ray-transparent material and the second x-ray-transparent material include the same attenuation properties for x-ray radiation.

8. The patient support device of claim 1, wherein the second x-ray-transparent material is at least one of configured elastically to compensate for a change in volume occurring in one of the phase transitions or for promoting a uniform distribution of a material strength of the first x-ray-transparent material, comprises at least one web embodied for form stabilization and having through openings for the first x-ray-transparent material, or is only flexible at target hinge points.

9. The patient support device of claim 1, wherein the at least one induction device is configured to produce an application, a removal of energy, or the application and the removal of energy by at least one of heat, cold, or electrical current.

10. The patient support device of claim 1, further comprising:
    a preparation device for the patient couch, the preparation device comprising
       at least one contact surface for the patient couch; and
       at least one adjusting device acting on the contact surface.

11. The patient support device of claim 10, wherein the at least one of the at least one adjusting device is a hinge for tilting a portion of the contact surface against an adjacent portion of the contact surface.

12. The patient support device of claim 11, wherein the preparation device is a frame.

13. The patient support device of claim 1, wherein in a leg area, the patient couch comprises a cut running in a longitudinal direction for independently positioning the bearing surface for both legs of a patient in the deformable state.

14. The patient support device of claim 1, wherein the support configured as at least one pillar may be adjustable at least in terms of its height.

* * * * *